United States Patent [19]

Fogarty et al.

[11] Patent Number: 5,876,413
[45] Date of Patent: *Mar. 2, 1999

[54] METHODS AND DEVICES FOR BLOOD VESSEL HARVESTING

[75] Inventors: Thomas J. Fogarty; George D. Hermann, both of Portola Valley; Allan R. Will, Atherton, all of Calif.

[73] Assignee: General Surgical Innovations, Inc., Palo Alto, Calif.

[*] Notice: This patent issued on a continued prosecution application filed under 37 CFR 1.53(d), and is subject to the twenty year patent term provisions of 35 U.S.C. 154(a)(2).

The term of this patent shall not extend beyond the expiration date of Pat. No. 5,601,581.

[21] Appl. No.: 798,048

[22] Filed: Feb. 10, 1997

Related U.S. Application Data

[63] Continuation of Ser. No. 444,424, May 19, 1995, Pat. No. 5,601,581.

[51] Int. Cl.⁶ .................................................... A61B 17/22
[52] U.S. Cl. ............................................ 606/159; 606/157
[58] Field of Search ................................. 606/159, 157, 606/158, 170, 167, 108

[56] References Cited

U.S. PATENT DOCUMENTS

| | | | |
|---|---|---|---|
| 4,271,839 | 6/1981 | Fogarty et al. | 128/344 |
| 4,479,497 | 10/1984 | Fogarty et al. | 128/344 |
| 4,493,711 | 1/1985 | Chin et al. | 604/271 |
| 4,597,389 | 7/1986 | Ibrahim et al. | 606/159 |
| 5,346,503 | 9/1994 | Chow | 606/170 |
| 5,352,219 | 10/1994 | Reddy | 606/1 |
| 5,366,478 | 11/1994 | Brinakerhoff et al. | 606/159 |
| 5,373,840 | 12/1994 | Knighton | 128/4 |
| 5,397,333 | 3/1995 | Knoepfler | 606/170 |
| 5,423,842 | 6/1995 | Michelson | 606/167 |
| 5,522,824 | 6/1996 | Ashby | 606/159 |
| 5,591,183 | 1/1997 | Chin | 606/159 |
| 5,601,581 | 2/1997 | Fogarty et al. | 606/159 |
| 5,611,814 | 3/1997 | Lorenc | 606/213 |
| 5,667,480 | 9/1997 | Knight et al. | 600/212 |

*Primary Examiner*—Michael Powell Buiz
*Assistant Examiner*—Kevin Truong
*Attorney, Agent, or Firm*—Lyon & Lyon LLP

[57] ABSTRACT

Methods and devices for harvesting veins or other elongate structures from the body are disclosed. The disclosed methods and devices allow vein harvesting using endoscopic procedures. A working space is created over a vein using standard endoscopic procedures and a side-hooked wire is inserted into the working space and twisted to insert the side-hook under the vein. The wire is then pulled or drawn along the vein to separate the vein from the surrounding tissue. In an alternative embodiment, vein separation is accomplished by threading a soft rubber tube under the vein, and then pulling the tube along the vein. In other embodiments, the working space is created with everting balloons.

6 Claims, 12 Drawing Sheets

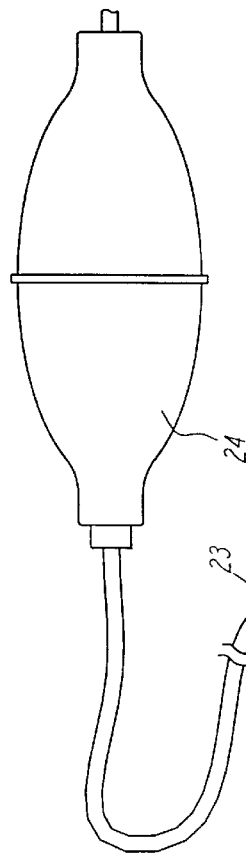
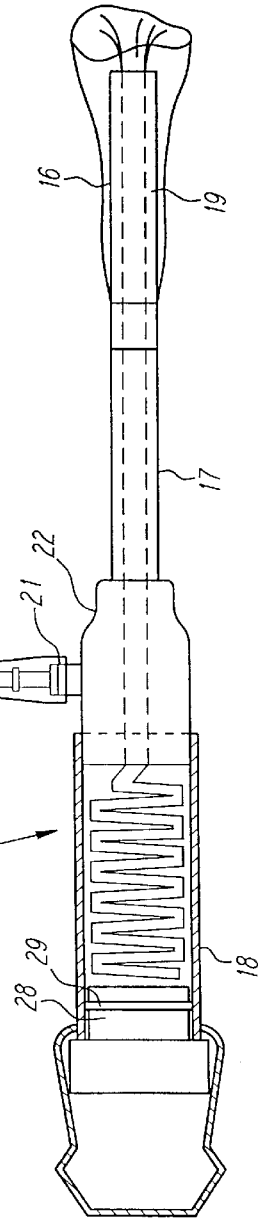
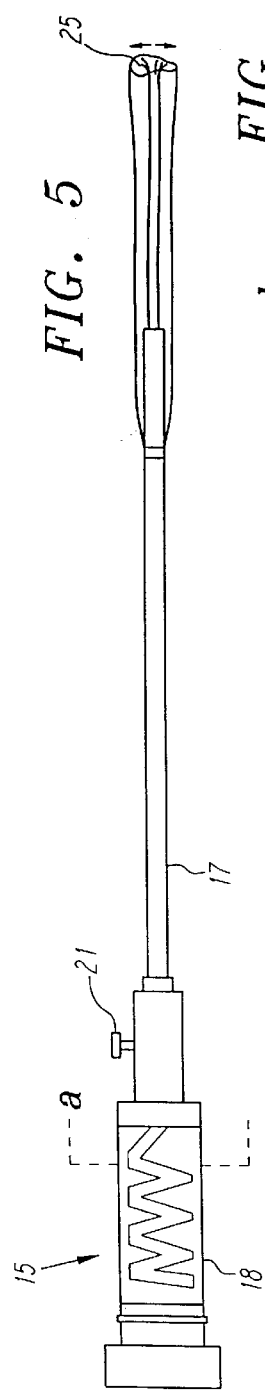
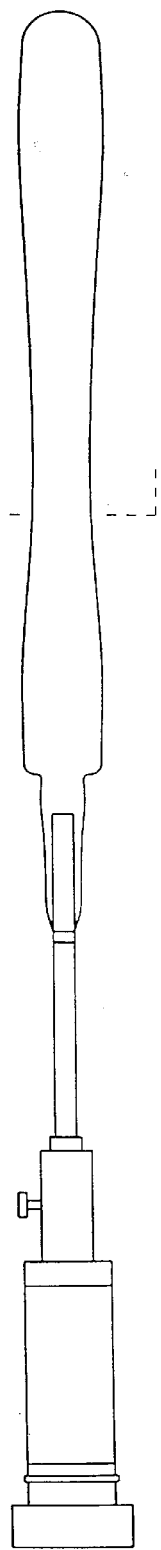
FIG. 4
FIG. 5
FIG. 6

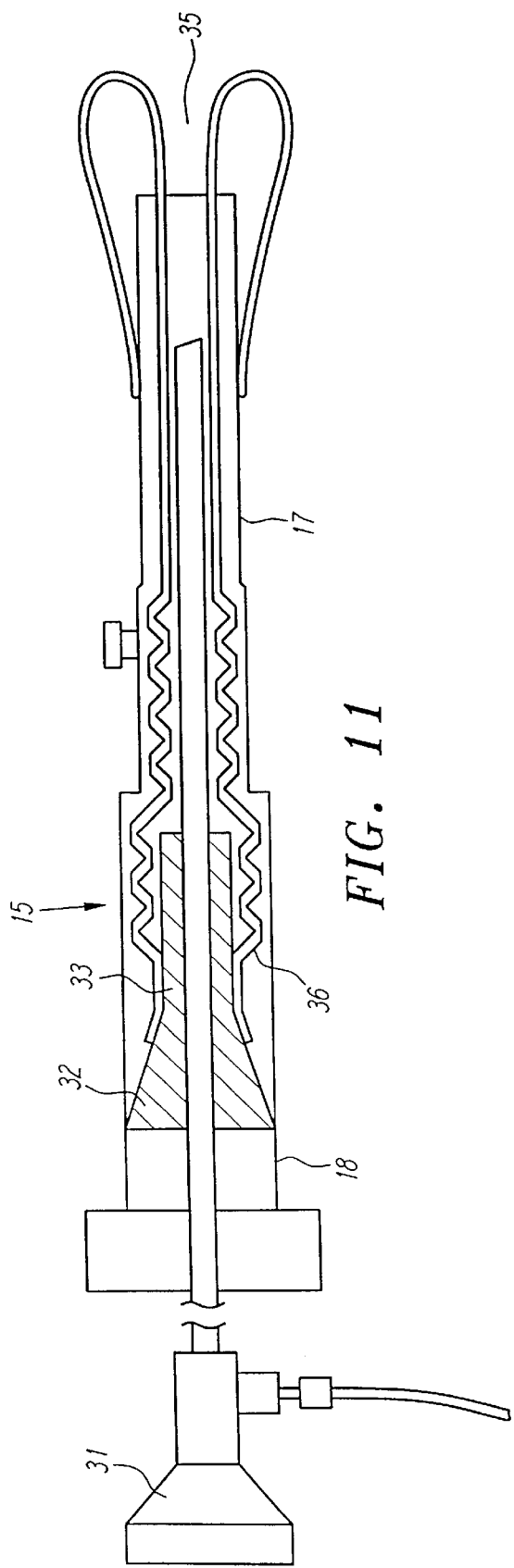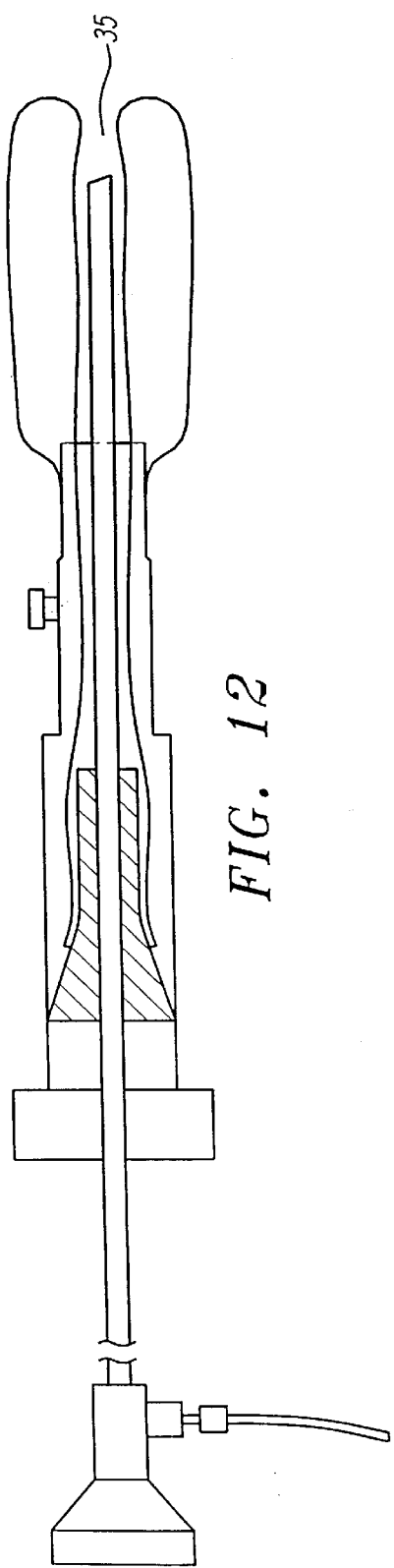

METHODS AND DEVICES FOR BLOOD VESSEL HARVESTING

CROSS REFERENCE TO RELATED APPLICATION

This is a continuation of U.S. application Ser. No. 08/444,424, filed on May 19, 1995, now U.S. Pat. No. 5,601,581. The priority of this prior application is expressly claimed and its disclosure is hereby incorporated by reference in its entirely.

FIELD OF THE INVENTION

This invention relates to methods and devices for endoscopic surgery, in particular to methods and devices for dissecting tissue to create a working space for endoscopic instruments.

BACKGROUND OF THE INVENTION

Numerous surgical procedures have been developed to replace arteries that have become blocked by disease. The aortocoronary bypass surgery is perhaps the most important of these bypass operations. The coronary arteries supply blood to the heart. As a result of aging and disease, coronary arteries may become blocked by plaque deposits, stenosis, or cholesterol. In some instances, these blockages can be treated with atherectomy, angioplasty, or stent placement, and coronary bypass surgery is not required. Coronary bypass surgery is required when these other methods of treatment cannot be used or have failed to clear the blocked artery. In coronary bypass surgery, a vein is harvested from elsewhere in the body and grafted into place between the aorta and the coronary artery beyond the point of blockage. An illustration of this surgery is shown in FIG. 1, which shows the heart 1 and the right anterior coronary artery 2 and the left anterior coronary artery 3 which supply blood to the heart 1. The right anterior coronary artery 2 is blocked in its proximal segment at 2a, as shown. This blockage has been bypassed by grafting a segment of vein 4 between the aorta 5 and the distal segment 2b of the right anterior coronary artery 2. Similarly, the left anterior coronary artery 3 may be blocked, and may require bypass with a length of vein 4a between the aorta and the distal segment 3b of the left anterior artery. The operation requires access to the heart, which means that the chest cavity must be opened completely.

The coronary bypass surgery requires a length of vein or artery for the graft. It is preferred to use a vein taken from the patient undergoing the bypass surgery. The patient is a ready source of suitable veins that will not be rejected by the body after transplantation and grafting onto the aorta and coronary artery. The saphenous vein in the leg is the best substitute for small arteries such as the coronary arteries, and it is the preferred vein for use in coronary bypass surgery. This is because the saphenous vein is typically 3 to 5 mm in diameter, about the same size as the coronary arteries. Also, the venous system of the legs is sufficiently redundant so that after removal of the saphenous vein, other veins that remain in the leg are adequate to provide adequate return blood flow. The cephalic vein in the arm is an alternative that is sometimes used.

A typical operation previously required to harvest the saphenous vein is illustrated in FIG. 2. The surgeon cuts into the leg to allow access to the saphenous vein 6 and cuts the vein 6 from the leg. To expose the saphenous vein 6, the surgeon makes a series of incisions from the groin 7 to the knee 8 or the ankle 9, leaving one or more skin bridges 10 along the line of the incisions. (Some surgeons make one continuous incision from the groin to the knee or ankle.) Handling of the vein 6 must be kept to a minimum, but the vein 6 must be removed from connective tissue that requires some force to remove. After exposing the vein 6, the surgeon grasps it with his fingers while stripping off the surrounding tissues with dissecting scissors or other scraping instruments. The surgeon uses his fingers and blunt dissection tools to pull and lift (or mobilize) the vein 6 from the surrounding tissue. The vein 6 is mobilized or pulled as far as possible through each incision. To reach under the skin bridges 10, the surgeon lifts the skin with retractors and digs the vein free. While stripping the vein, the surgeon will encounter the various tributary veins that feed into the saphenous vein 6. These tributaries must be ligated and divided. To divide and ligate tributaries that lie under the skin bridges 10, the surgeon may need to cut one end of the saphenous vein 6 and pull it under the skin bridge 10 to gently pull the vein 6 out from under the skin bridge 10 until the tributary is sufficiently exposed so that it may be ligated and divided. When the vein 6 has been completely mobilized, the surgeon cuts the proximal and distal ends of the vein 6 and removes the vein 6 from the leg. After removal, the vein 6 is prepared for implantation into the graft site, and the long incisions made in the leg are stitched closed.

The procedure described above can be used to harvest veins for a femoral popliteal bypass, in which an occluded femoral artery is bypassed from above the occlusion to the popliteal artery above or below the knee. The procedure can also be used to harvest veins for the revascularization of the superior mesenteric artery which supplies blood to the abdominal cavity and intestines. In this case, the harvested vein is inserted between the aorta to the distal and patent (unblocked) section of the mesenteric artery. For bypass grafts of the lower popliteal branches in the calf, the procedure can be used to harvest the umbilical vein. The harvested vein can also be used for a vein loop in the arm (for dialysis) between the cephalic vein and brachial artery. The procedures may be used also to harvest veins for femoral-tibial, femora-peroneal, aorto-femoral, and iliacfemoral by-pass operations and any other by-pass operation.

As can be seen from the description of the harvesting operation, the harvesting operation is very traumatic in its own right. In the case of coronary artery bypass, this operation is carried out immediately before the open chest operation required to graft the harvested vein into the coronary arteries. The vein harvesting operation is often the most troublesome part of the operation. The long incisions created in the leg can be slow to heal and very painful. Complications resulting from the vein harvesting operation can also hinder the patient's recovery from the entire operation.

The method of vein harvesting presented herein is accomplished with endoscopic procedures. This allows the veins to be harvested in an operation that requires only a few small incisions. Endoscopic surgical techniques for operations such as gall bladder removal and hernia repair are now common. The surgeon performing the operation makes a few small incisions and inserts long tools, including forceps, scissors, and staplers, into the incision and deep into the body. Viewing the tools through an endoscope or laparoscope, or a video display from the endoscope, the surgeon can perform all the cutting and suturing operations necessary for a wide variety of operations. The procedures are also referred to as laparoscopic surgery, minimally invasive surgery or video-assisted surgery. References to endoscopic surgery and endoscopes below is intended to encompass all these fields, and all operations described below with reference to endoscopes can also be accomplished with laparoscopes, gastroscopes, and any other imaging devices which may be conveniently used.

Minimally invasive procedures for vein removal have been proposed. Knighton, Endoscope and Method for Vein Removal, U.S. Pat. No. 5,373,840 shows a method of cutting the saphenous vein at one end, and grasping the vein with graspers or forceps, then sliding a ring over the vein while holding it. Knighton uses a dissecting tool with an annular cutting ring, and requires that the saphenous vein be overrun or progressively surrounded with the dissecting tool and the endoscope, so that after the endoscope has been inserted as far as it will go, the entire dissected portion of the vein has been pulled into the lumen of the endoscope. As shown in FIGS. 1 and 10 of Knighton, the method requires deployment of the forceps inside the annular dissection loop, and it requires deployment of the loop and graspers inside the endoscope lumen. The blood vessel must be cut and grasped by the forceps before it can be dissected by the dissecting ring.

The method of vein harvesting presented below may use a balloon to assist in dissecting the harvested vein. An everted balloon stored inside a cannula or trocar may be inserted through one of the small incisions and inflated so that it everts out the end of the cannula and forces its way along the vein to create a tunnel.

SUMMARY OF THE INVENTION

The methods and devices presented herein allow surgeons to harvest veins without making long incisions as previously required. The procedure is a minimally invasive procedure which requires just a few small incisions, one at either end of the saphenous vein. The procedure is accomplished with endoscopic or laparoscopic instruments under the guidance of an endoscope. After making the incisions, the surgeon inserts a tunneling instrument or blunt dissector into one incision and advances or pushes along the saphenous vein to make a small tunnel alongside the saphenous vein. The surgeon then inserts the long balloon described below in the tunnel and inflates the balloon to enlarge and further propagate the tunnel. The surgeon may use the balloon to dissect the fat and skin overlying the saphenous vein away from the vein, and also to enlarge the tunnel to an appropriate size. When the tunneling is completed, the surgeon removes the balloon and seals the tunnel at both ends. The surgeon then injects carbon dioxide, nitrous oxide or other suitable gas into the tunnel at sufficient pressure (typically 5–15 mmHg) to inflate the tunnel and create room for laparoscopic instruments. The surgeon then inserts an endoscope or laparoscope through the seal to provide a view of the procedure, and inserts an endoscopic vein harvesting device described in detail below. With the vein harvester in place, the surgeon manipulates the vein harvester to strip the connective tissue from the vein, identify and cut side branches, and remove the vein from its channel in the leg. After the vein is loosened or dissected free from its channel in the leg, the surgeon can cut the proximal and distal ends and easily pull the vein from the leg. The small skin incisions are stitched so they may heal. The small incisions heal much more readily, with fewer complications and far less pain, than the operation now in use.

The surgeon operating with the vein harvesting device has a choice of tunneling instruments. A typical blunt dissection is performed with long stiff rod with a round tip, and the tip may be enlarged. The surgeon may also use a device referred to as a peanut, which is long rod with a soft fabric or foam tip. These devices are used to create a small tunnel, and then the balloon may be inserted to enlarge the tunnel. The balloon dissector described below allows the tunneling operation to be accomplished by the balloon, thus allowing easier and less traumatic creation of the initial tunnel, and also permitting the surgeon to create the enlarged tunnel with this single device. The device may be used as an alternative to the other methods of enlarging the tunnel.

BRIEF DESCRIPTION OF THE DRAWINGS

Reference is made to the accompanying drawings, in which like reference numerals indicate like parts, and in which are shown illustrative embodiments of the invention from which its novel features and advantages will be apparent to those of ordinary skill in the art.

FIG. 4 shows the balloon dissector with the balloon housed in the handle.

FIG. 5 shows the balloon dissector with the balloon in its inflated state.

FIG. 6 shows the balloon cannula with the balloon fully inflated.

FIG. 11 shows a balloon dissector with a lumen.

FIG. 12 shows the balloon dissector with lumen with the balloon fully inflated.

DETAILED DESCRIPTION OF A PREFERRED EMBODIMENT

Figure 1:
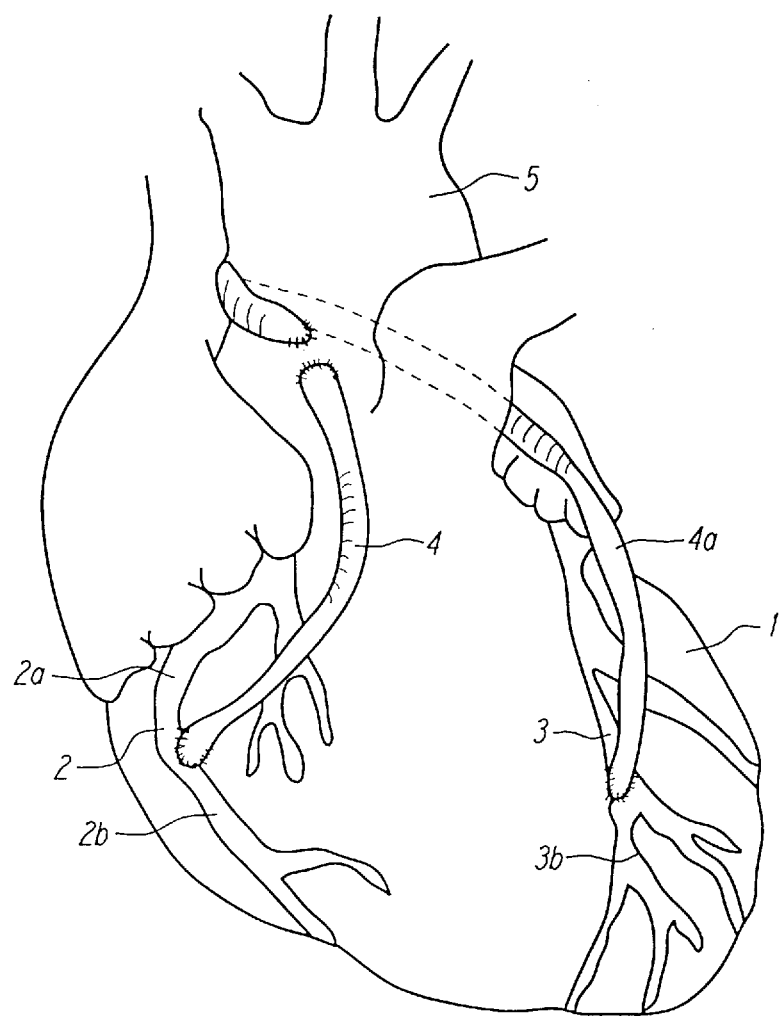
FIG. 1 is a front view of the heart showing a vein grafted from the aorta to the right anterior coronary artery, bypassing the proximal segment of the right anterior coronary artery.
Figures 2, 3:
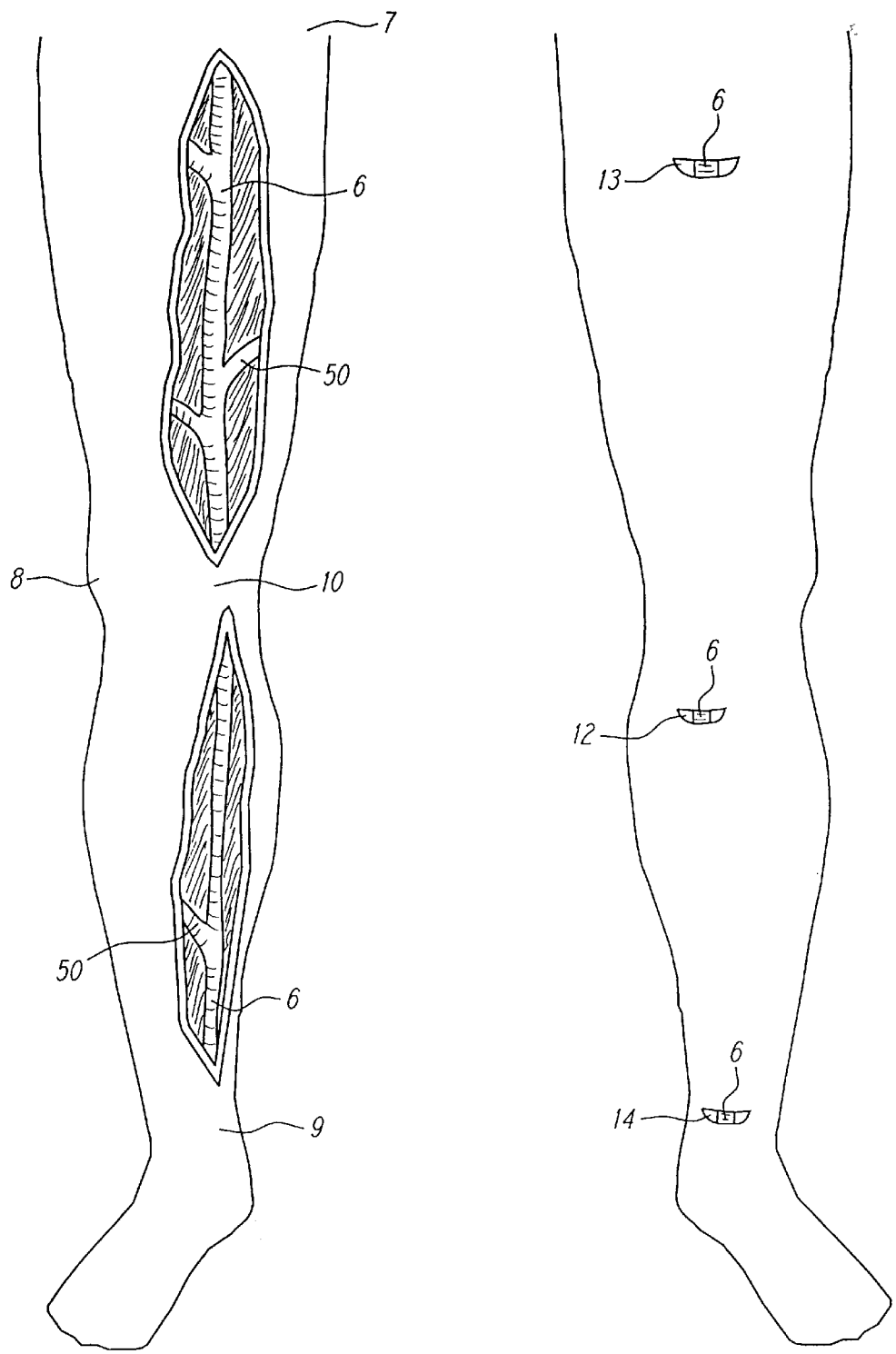
FIG. 2 is a view of the leg showing the incisions necessary for harvesting the saphenous vein using currently known methods.
FIGS. 3 and 3a are views of the leg showing the incisions necessary for harvesting the saphenous vein using the methods presented herein.

The methods and devices presented herein take advantage of laparoscopic procedures to lessen the trauma of vein harvesting operations. Instead of making an incision along or over the entire length, or essentially the entire length of the vein to be harvested, the procedure may be conducted with only a few small incisions. All that is needed is a working space large enough to allow the surgeon to use the tool and view the operation through a laparoscope. In the preferred embodiment of the method, the surgeon creates a working space under the skin and over the saphenous vein using laparoscopic techniques. The surgeon makes several small incisions as shown in FIG. 3, to expose the saphenous vein. These incisions are referred to as cut-downs. A distal incision 12 near the knee and a proximal incision 13 at the groin are preferred. If the entire length of the saphenous vein is to be harvested, an additional incision 14 can be made close to the ankle. In FIG. 3, the saphenous vein 6 can be seen through the cut-downs 12, 13 and 14. It will be apparent from the description that the use of three or four incisions used to harvest the entire saphenous vein 6 is merely a matter of convenience, and those particularly skilled in laparoscopic procedures may require fewer incisions, and also smaller incisions may be used.

After making the incisions, the surgeon inserts a blunt tunneling tool (not shown) into one incision and pushes it along the saphenous vein towards the other incision. The tunneling creates a tunnel or channel running along the saphenous vein 6. The tunnel may be expanded by insertion of the balloon described herein, which can be inflated to expand or propagate the tunnel further along the saphenous vein 6.

FIG. 4 shows the balloon dissector or balloon trocar 15 in its uninflated state, with the balloon 16 packed inside the device. The balloon 16 is a non-elastomeric balloon or bladder. The balloon trocar 15 comprises a balloon 16, a trocar portion 17 and a balloon housing portion 18. The trocar portion 17 is cylindrical, with a circular cross-section, but may be made in oval cross-section or in other cross-sections. The balloon 16 is sealed to the distal tip 19 of the trocar portion 17 of the balloon trocar 15. The balloon material is wrapped over the distal tip 19 and sealed to the outside of the trocar portion 17. The balloon may be sealed to the trocar with adhesives, or it may be heat sealed, banded or taped (cellophane tape, such as Scotch™ adhesive tape, is sufficient) or sealed in any suitable manner to the trocar 17. The balloon 16 then extends back through the trocar, to the proximal balloon housing portion 18 of the balloon trocar 15. When used for tunneling along the saphenous vein 6, the balloon is approximately 60 centimeters long. The trocar or cannula is most conveniently 10–20 centimeters long, so that the excess length of the balloon 16 is folded as shown inside the balloon housing portion 18 of the balloon trocar 15. The balloon is sealed at its distal end, referring here to the distal end as determined when the balloon 16 is everted outside of the balloon housing 18. The balloon 16 may be formed by extrusion or by heat sealing or gluing a number of pieces of material together.

The balloon trocar 15 is fitted with an inflation port 21, which may be located anywhere on the trocar portion 17 or balloon housing 18. In FIG. 4, the inflation port is shown affixed to the balloon housing 18 at its proximal end near a necked-down portion 22 between the housing portion 18 and the trocar portion 17. The inflation port 21 comprises a tube establishing a pathway for liquid or gas to be injected into the balloon trocar 15 to inflate the balloon 16. A convenient length of flexible tubing such as tygon tubing 23 can be used to communicate an inflation fluid to the balloon 16 from a bladder pump 24 or large syringe capable of injecting liquid or gas into the balloon housing 18. Sterile saline solution is the preferable inflation medium for medical applications. Alternately, air, $CO_2$, or even foam or other substances may be injected to cause inflation.

Upon injection of liquid or gas into the balloon housing 18, the pressure created inside the housing 18 forces the balloon 16 to evert out through the trocar portion 17. The segment of the balloon 16 stored in the housing portion 18 gradually rolls forward (distally) and outside the trocar 17, rolling over itself and turning itself inside out, or everting, and pushing forward. As shown in FIG. 5, the balloon 16 has everted under pressure, and the leading edge 25 pushes forward, unrolling from the inside, to advance through body tissue. Eventually, the balloon 16 completely unfolds or everts to create a long cylindrical balloon 16. The balloon 16 may be folded in a variety of ways, including the fan fold shown in FIG. 5, or with accordion folds as shown in FIG. 11, or it may be rolled inside the cannula.

Figure 7:
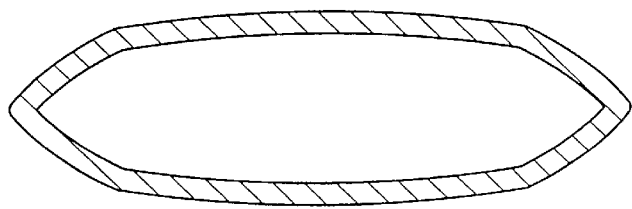
FIG. 7 shows a cross-section of the inflatable membrane in its uninflated state.
Figure 8:
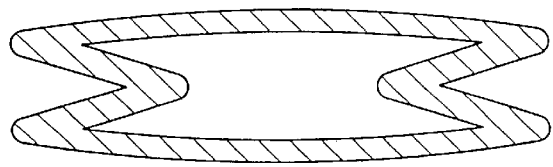
FIG. 8 shows a cross-section of the inflatable membrane in its inflated state.

The fully inflated and everted balloon 16 is showed in FIG. 6. The inflated diameter of the balloon 16 is more useful when it is larger than the diameter of the trocar 17. This allows for the creation of a tunnel that is wider than the trocar 17. The balloon diameter or radial cross-section of the balloon 16 may also be smaller than the diameter of the trocar 17, and may be adjusted to create a tunnel of any desired size. The balloon 16 may be pleated, or folded like a brown paper bag, or folded in any other manner which facilitates eversion and packing in the housing 18. The cross-section of the uninflated balloon 16 along section a of FIG. 5 is shown in FIG. 7, and the cross section of the inflated balloon along cross section b of FIG. 6 is shown in FIG. 8. The balloon 16 is preferably non-elastic, so that it will not expand uncontrollably into the softest body tissue or weakest tissue plane. Acceptable materials include polyethylene and other medical grade plastics. A slight degree of elasticity is acceptable, and even complete elasticity may be acceptable where there is no danger of the balloon 16 expanding in an unwanted or unpredictable shape.

Figure 9:
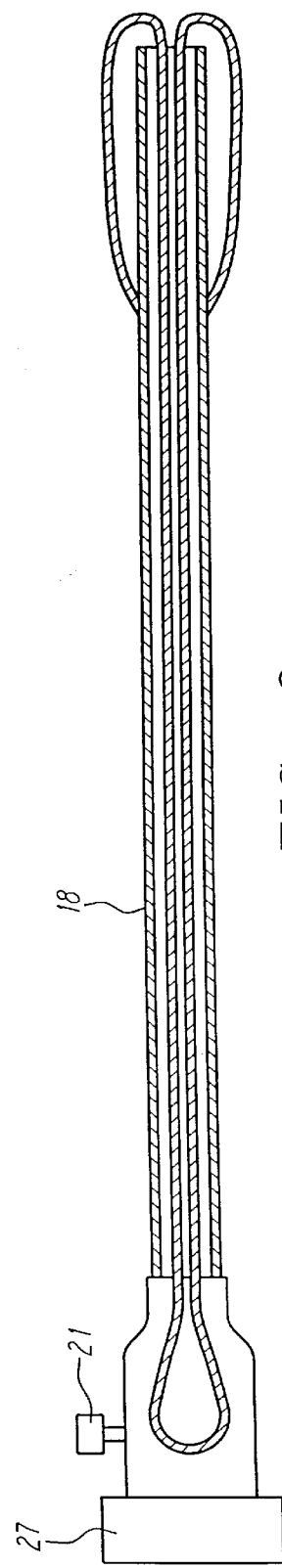
FIG. 9 shows a cross section of a simplified balloon cannula.

FIG. 9 shows an alternate embodiment of the balloon trocar in which the excess length of the balloon is stored inside a longer housing so that it need not be folded. The balloon housing 18 is longer than the balloon housing 18 shown in FIG. 4. The balloon is sealed at the distal tip of the trocar in the same manner shown in FIG. 4, and the distal end of the balloon is sealed. The inflation port 21, again, may be placed in any convenient place on the balloon trocar. The proximal end of the balloon housing is sealed by an end cap 27, which can be integrally formed with the balloon trocar. The end cap can also be removable and include a threaded cap which is screwed onto the end of the balloon housing and fitted with a gasket to prevent leakage. As shown in FIG. 4, the end cap can also include a plug 28 which fits tightly into the balloon housing, and the plug may be provided with an O-ring 29 to help maintain the seal on the housing. Upon inflation, the balloon everts or unfolds out the distal tip of the balloon trocar. The balloon forces itself between the body tissues to be dissected or tunneled through in the same manner as described above.

Figure 10:
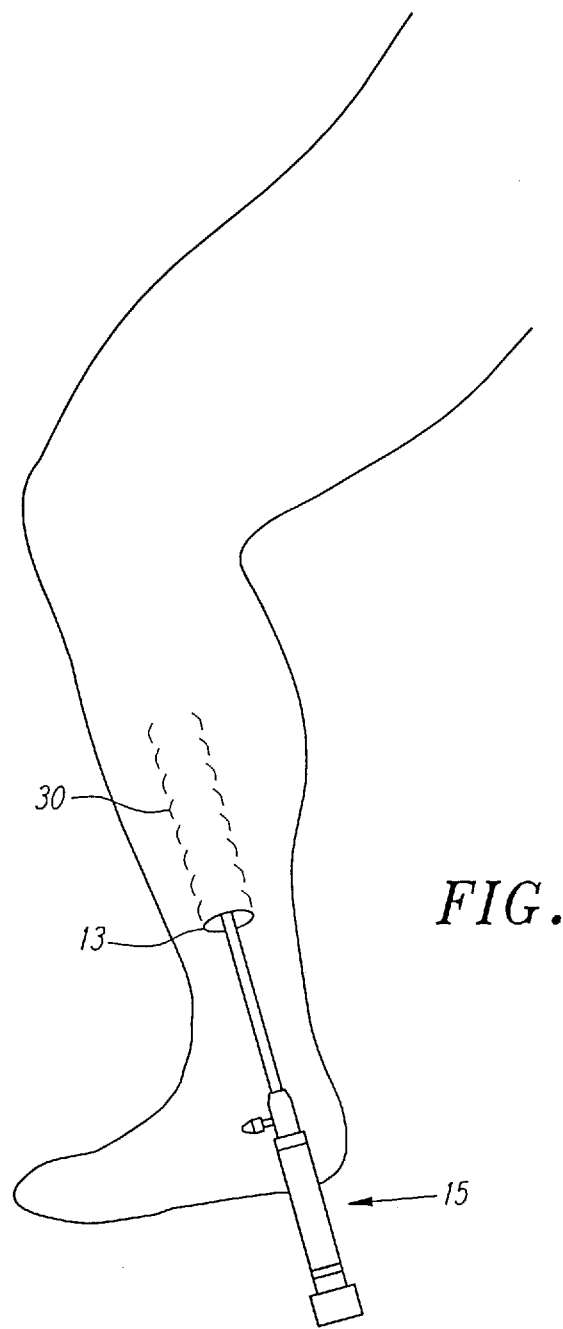
FIG. 10 shows the balloon cannula inserted into the leg of a patient.

FIG. 10 shows the balloon trocar inserted into the ankle incision or cut down 13. The surgeon inserts the balloon into the incision and points it in the direction of the tunnel that he wants to make. In FIG. 10, the balloon trocar 15 is inserted as it would be if the surgeon wanted to create or enlarge a tunnel along the saphenous vein, going up the leg. Once the surgeon has put the balloon trocar in place, the balloon is ready for inflation. The surgeon can inflate the balloon and allow it to evert into the leg. The balloon will follow a tunnel previously created by the surgeon with a blunt dissecting tool, if the surgeon has chosen to create the tunnel with another tool and use the balloon to enlarge that tunnel. The balloon will also create its own tunnel, without the need to create an initial tunnel over the entire length of the saphenous vein. The surgeon can make a small starter tunnel, using a finger or tool to get the tunnel started, and then the surgeon can insert the balloon and inflate it. Upon eversion or unrolling, the balloon will force its way into the leg and propagate along the tissue boundary between the saphenous vein and the fat and skin layer above the vein. Eversion and propagation of the balloon creates a tunnel over the saphenous vein, or, in medical terms, superior to the saphenous vein. As the balloon propagates along the vein, it raises the skin over the balloon, creating a bubble or blister 30 which indicates that the balloon is everting along the vein, and has not taken some errant course. As the balloon propagates up the leg, the surgeon may guide it by pushing the tip of the balloon with his finger, through the skin without puncturing the skin. In this manner, the balloon gently forces its way between the layers of body tissue and pushes them apart to form the enlarged tunnel necessary for endoscopic or laparoscopic surgery on the saphenous vein.

The balloon dissector can be used in other procedures besides dissection for vein harvesting, and its description in that environment is intended to be illustrative of the device. The device can be used in any procedure for dissection, separating or retracting body tissue. The balloon trocar 15 may be made in varying sizes and lengths, so that it can be used to create passageways for laparoscopic surgery. After the passage is created, whether by the balloon or other means, the balloon trocar may be used to hold passageways open to allow laparoscopic instruments to be used in front of the distal end or leading edge of the everting balloon. These instruments may be inserted through the lumen of the balloon trocar 15, or they may be inserted through other access ports so that the balloon is used only to hold body tissue out of the way of these instruments as they are used. Additionally, the device may be used to hold an endoscope or laparoscope in a fixed and stable position within the body, so that the video display which the surgeon watches remains stable.

As described above, the balloon trocar 15 is used for dissection or tunneling in a semi-blind manner. When used in the leg, the propagation of the balloon can be observed by watching skin rise as the balloon tunnels under the skin. Because the location of the saphenous vein is well known and its exact course through the leg can be readily determined, the surgeon can be sure that the balloon is following the intended path along the saphenous vein. In some cases, however, the surgeon may wish to observe the propagation of the balloon endoscopically, or the surgeon may wish to observe various structures as the balloon everts past the structures. The everting balloon with a lumen 35 depicted in FIG. 11 can be used in this instance.

As shown in FIG. 11, the balloon trocar 15 may be constructed to allow passage of an endoscope 31 or other instrument through the balloon. The balloon housing 18 and trocar portion 17 of the device may be similar to the comparable structure shown in FIG. 4. The balloon is sealed to the distal tip of the trocar portion 17, and is also sealed to the proximal end of the balloon housing 18 by sealing the balloon to the sliding piston seal or sliding plunger 32. The sliding piston seal 32 fits tightly against the inside of the balloon housing 18 to create an air tight seal. A guide tube 33 is attached to the sliding piston 32 to facilitate sliding the endoscope through the lumen 35 provided in the balloon. Alternatively, in the configuration shown in FIG. 13, the balloon comprises a tube of non-elastic material with a short length of cuff rolled back at each end and folded over the proximal edge and sealing it to the outside of the balloon housing 18. The balloon housing 18 may be provided with an end cap 27 to prevent backward eversion of the balloon, and the end cap 27 may be provided with a port 34 which accommodates the endoscope 31. Any other suitable sealing means may be used. FIG. 12 shows the balloon in its fully extended state with the lumen large enough for an endoscope 31 to be inserted through the inside of guide tube 33. With the balloon inflated or deflated, an endoscope can be inserted through the lumen 35, as shown in FIGS. 11 and 12.

Figure 13:
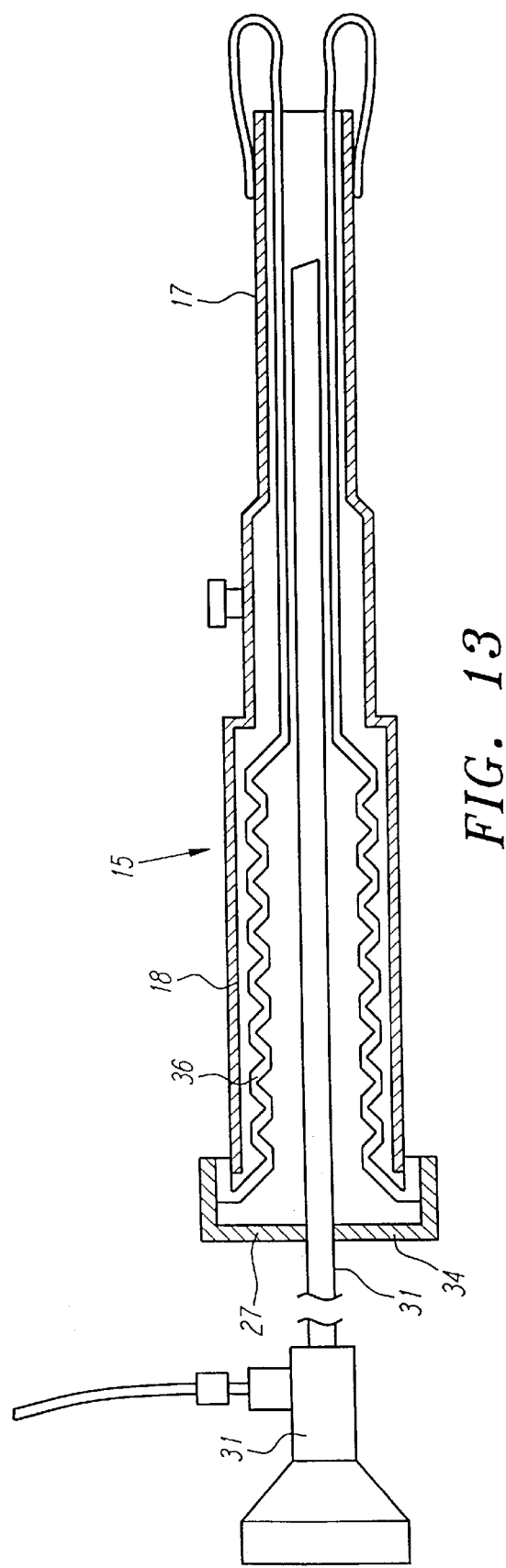
FIG. 13 shows an alternative embodiment of the balloon dissector with a lumen.

Before the balloon is inflated to cause eversion which is used for tunneling or dissection or retraction of body tissue, it is folded accordion style inside the balloon housing portion 18 of the balloon trocar 15. The excess length is held inside the housing in this manner until the balloon is everted under pressure. The accordion folds 36 can be made without a guide tube 33, as shown in FIG. 13, or with a guide tube 33 as shown in FIGS. 11 and 12. Alternatively, the endoscope or other instrument used within the lumen 35 may be used as the guide tube 33. The guide tube 33 can be integral with the end cap, or it can be mounted on a fixed or sliding plunger, annular seal, sealing ring or piston seal 32. Provision of a sliding plunger 32 allows longer deployment of the balloon outside the trocar portion 17.

While in use, the balloon may be inflated and everted partially or fully to cause it to tunnel through body tissue or between tissue planes. During eversion, the endoscope can be advanced to the leading edge or everted distal end of the balloon so that the surgeon can view the body tissue as it is dissected.

Figure 3A:
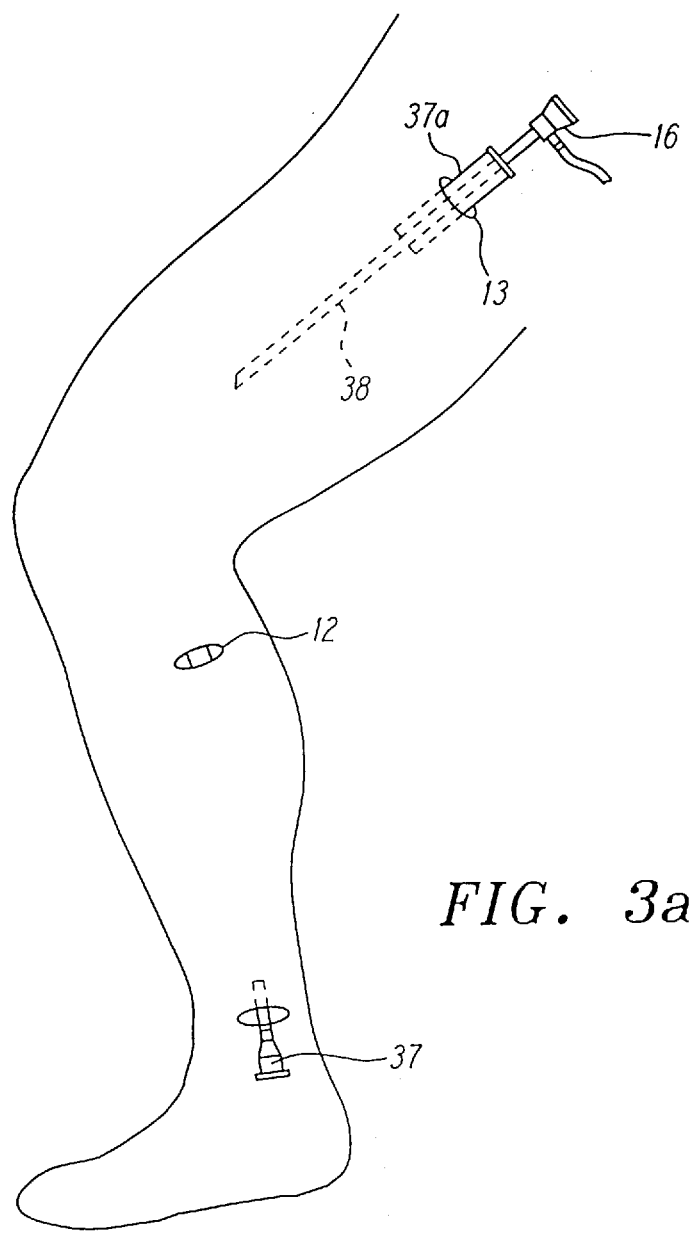

When the tunnel is of sufficient size, the incisions may be sealed with round trocars 37 and 37a, shown in place of FIG. 3a. The trocars are used to insert the various tools used in the procedure. One trocar is used to inject or infuse carbon dioxide ($CO_2$) or another gas (or liquid) into the tunnel in a procedure known as insufflation, which pressurizes the tunnel and keeps it open and expanded to make it easier to see inside the tunnel and easier to insert and manipulate an endoscope and instruments in the tunnel. Insufflation is accomplished with techniques generally known to endoscopic and laparoscopic surgeons. As can be seen in FIG. 3a, the insufflation creates an insufflated space 38 under the skin. An endoscope or laparoscope 16 is inserted into one of the trocars 37 or 37a, and as shown in FIG. 3a, is inserted into the groin incision 13 through trocar 37a. The endoscope permits the surgeon to view the tunnel, including the saphenous vein and connective tissue. The endoscope fits tightly into the trocar so a seal is accomplished between the endoscope and the trocar, and this helps maintain the pressure of the $CO_2$ gas. Also during insufflation, a vein harvesting tool may be inserted through the ankle trocar and operated to dissect and strip the vein and mobilize it. The incision may optionally be made at the knee, as indicated at reference numeral 12, or it may be made at both the knee and the ankle so that the balloon dissecting devices and vein harvesting devices can be used to dissect the saphenous vein first in the thigh and then in the calf, or vice-versa.

Figure 14:
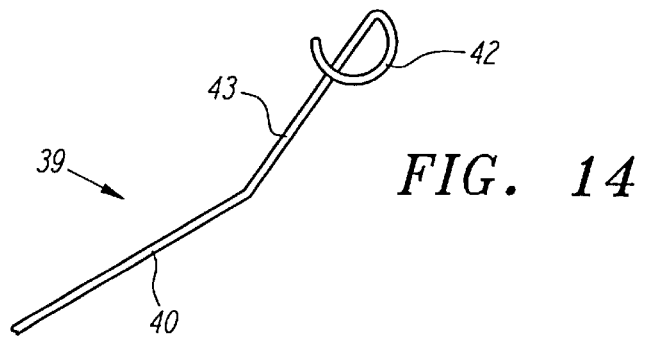
FIG. 14 shows a hooked vein harvester.

FIG. 14 shows a hooked vein harvesting tool 39 particularly suited for use in the methods described herein. The hooked vein harvesting tool 39 comprises a shaft or long slender rod 40 of stiff wire with a sideways hook 42 on one end. The hooked vein harvester 39 may be made of stainless steel, plastic, or other biocompatable material such as nitinol. The long segment or shaft 40 may have an offset or crooked segment 43 to set the hook off the axis established by the shaft 40. The sideways hook 42 is generally perpendicular to the axis of the shaft 40, or, in other words, the plane in which the hooks 42 lies is perpendicular to the line established by the shaft 40 or crooked section 43. Of course, the hook 42 need not be exactly perpendicular, and may be set at any angle which facilitates the ability to use the hook 42 as described herein. By twisting or rotating the shaft 40, the surgeon can slip the hook 42 under the exposed saphenous vein. The hook 42 may be provided with a pointed tip to enable it to puncture the connective tissue which covers the saphenous vein. The hook occupies an arc or radial segment of about 180 to 270 degrees so that the saphenous vein will lie inside the hook 42 when engaged by the hook 42. The diameter of the circle defined by the hook 42 is slightly larger than the diameter of the saphenous vein, so that the hook 42 can be easily slipped under the saphenous vein. When the hook 42 is safely around the saphenous vein, the surgeon can separate the vein from the surrounding tissue by pulling or pushing the shaft 40 and sliding the hook 42 along the saphenous vein. When a side branch is encountered, the hook will be blocked by the side branch, and can be used to expose the side branch for ligation and dividing it from the saphenous vein. When the entire length of the saphenous vein has been separated from the connective tissue, the vein can be grasped with laparoscopic grippers and pulled from the leg through the groin incision 13, the knee incision 12 or the ankle incision 14.

Figure 17A:
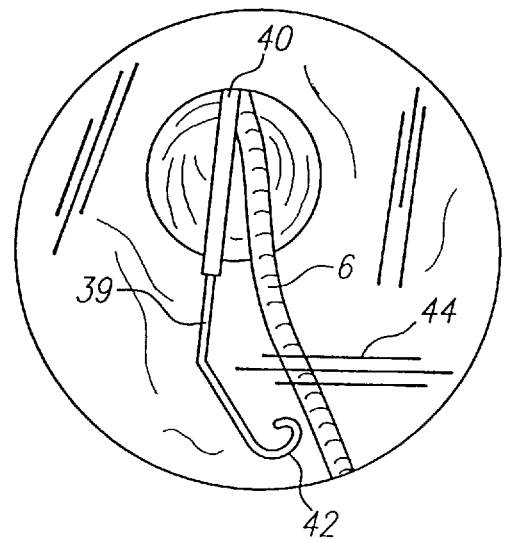
FIGS. 17a through 17c are laparoscopic views of the hooked vein harvester being placed around the saphenous vein.
Figure 17B:
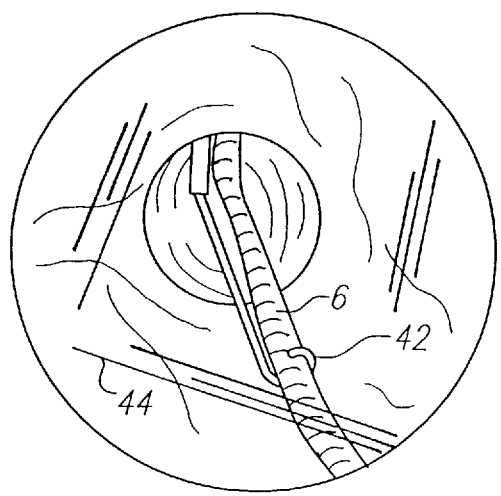
Figure 17C:
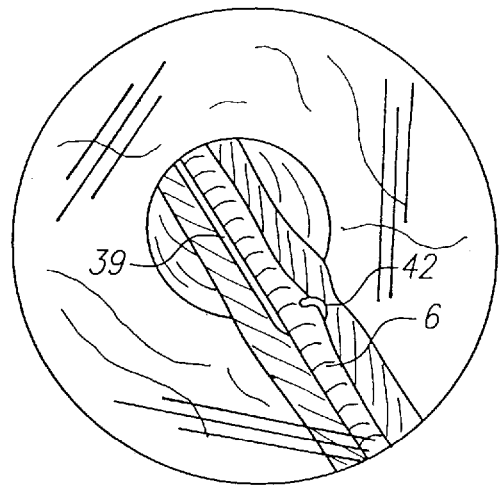

FIGS. 17a through 17c show the use of the hooked vein harvester 39 as viewed through an endoscope inserted through the groin incision 11. The saphenous vein 6 is seen lying in its channel surrounded by connective tissue 44. The hooked vein harvester 39 is shown as it would appear when inserted from the knee incision 12. The hook 42 appears in the foreground and the shaft 40 is receding toward the far end of the tunnel. In FIG. 17a, the hook 42 is in position at the upper end of the saphenous vein. In FIG. 17b, the shaft has been twisted or rotated by the surgeon so that the hook 42 is slipped under and around the saphenous vein from the connective tissue. In FIG. 17c, the surgeon has pulled the vein harvester 39, and perhaps rotated the hook 42 a bit more and pulled again, and freed or dissected the saphenous vein 6 from the connection tissue. The shaft 40 can be manipulated to lift or mobilize the saphenous vein 6 from the channel in which it lies. The shaft 40 can be pushed and pulled as necessary to separate or dissect the connective tissue from the vein 6.

Figure 18:
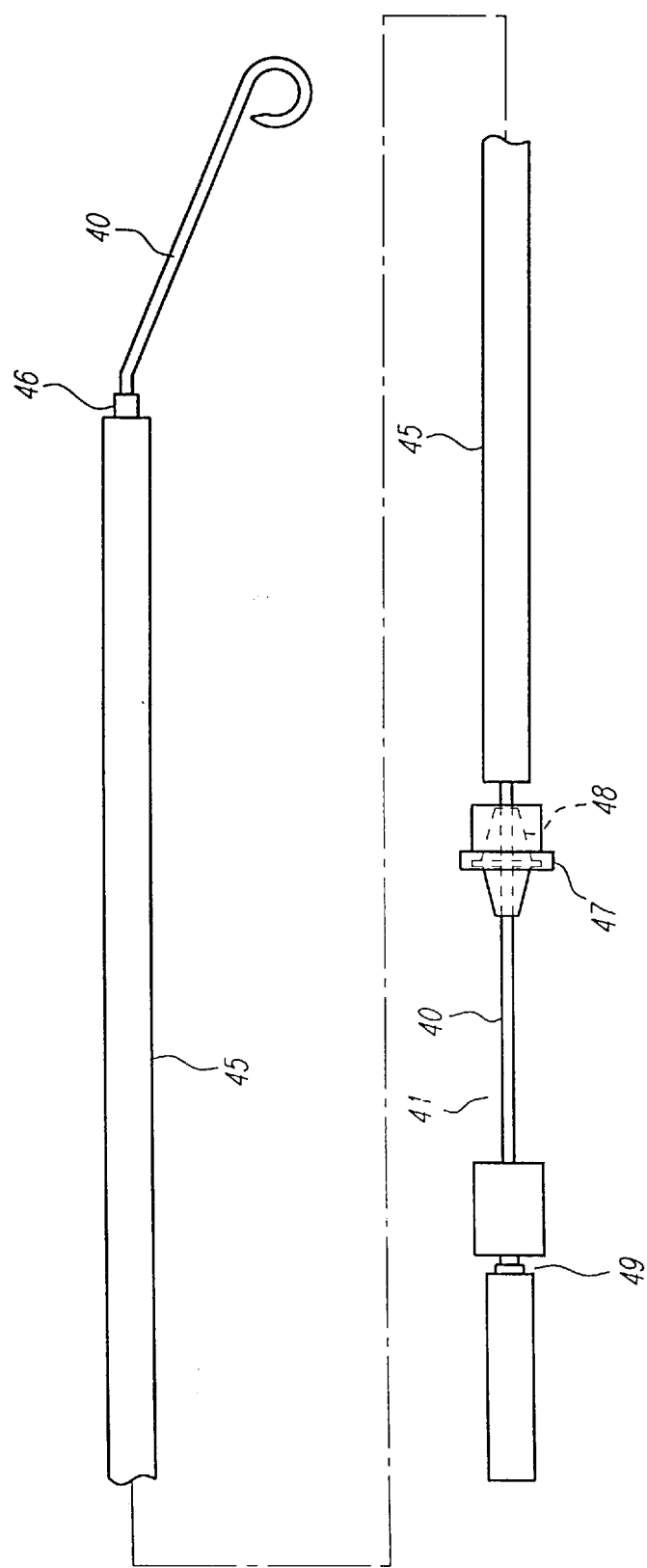
FIG. 18 shows the hooked vein harvester tool fitted with sealing tubes facilitating its use during insufflation.

Several other features of the device 39 are provided in order to make it more suitable for use in conjunction with the trocar and $CO_2$ insufflation. These features make it easier to deploy the vein harvester 39 through a standard trocar with an inside diameter which is larger than the wire 40. As shown in FIG. 18, a tube 45 surrounds the wire 40 for the greater portion of its length. At the distal end of the tube, an O-ring 46 or plastic sealing ring is fixed to the inside of the tube and fits closely around the shaft or wire 40. This seal 46 helps maintain the $CO_2$ pressure inside the tunnel so that the tunnel remains insufflated while the vein harvester 39 is in use. At the proximal end of the tube 45, a valve assembly 47 with a duckbill valve 48 inside fits tightly into the tube 45. The valve assembly 47 allows the wire 40 to pass through the duckbill valve 48, and the duckbill valve closes around the wire 40 to provide an additional seal around the wire 40. A second O-ring or plastic sealing ring can also be used to provide a second seal at the proximal end of the tube 45. To make handling of wire 40 easier, a handle 49 can be provided on the proximal end 41 of the wire 40. The handle shown in FIG. 18 is removable, but a fixed handle may be provided.

The saphenous vein has a number of tributary veins, shown at reference numeral 50 in FIG. 2, which carry venous blood into it. These tributaries must be tied off and cut off the saphenous vein before the saphenous vein can be removed. In medical terms, these tributaries must be ligated and divided. These tributaries can be readily identified with the vein harvester because the surgeon will feel the resistance while pulling and will not be able to pull the hook 42 through a tributary vein. When a tributary is encountered, the surgeon can use standard endoscopic and laparoscopic tools to close the tributaries and cut them from the saphenous vein. The tributaries can be separated from the vein after the entire vein is stripped, or the surgeon may choose to separate them as they are encountered.

Figure 15:
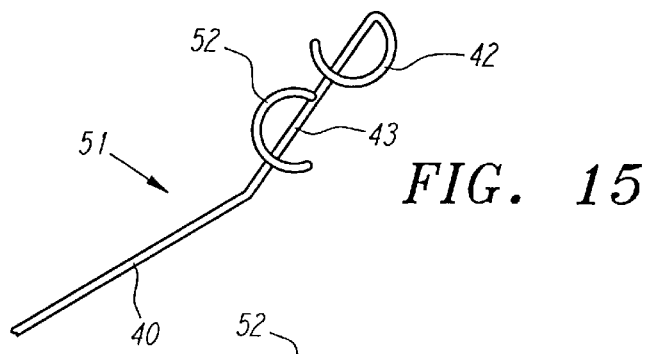
FIGS. 15 and 15a show a double hooked vein harvester.

FIG. 15 shows a double hooked vein harvester 51 with a shaft 40 and hook 42 at the distal end of the shaft 40, and a second hook 52 fixed to the shaft 40 just a short distance before the hook 42. This end of the shaft is referred to as the distal end because it is end that is inserted into the body. The handle end which remains outside the body is referred to as the proximal end. The second hook 52 is located a short distance proximal of the first hook 42. The proximal or second hook 52 opposes the first or distal hook 42, and extends from the shaft along a plane perpendicular to the shaft 40. Where the first hook 42 extends counterclockwise from the shaft 40, the second hook 52 extends clockwise from the shaft 40 so that the two hooks are in opposing relationship. The hook does not need to be exactly perpendicular, and needs only to be offset to a degree sufficient to allow it to engage the saphenous vein upon rotation toward the vein.

Figure 15A:
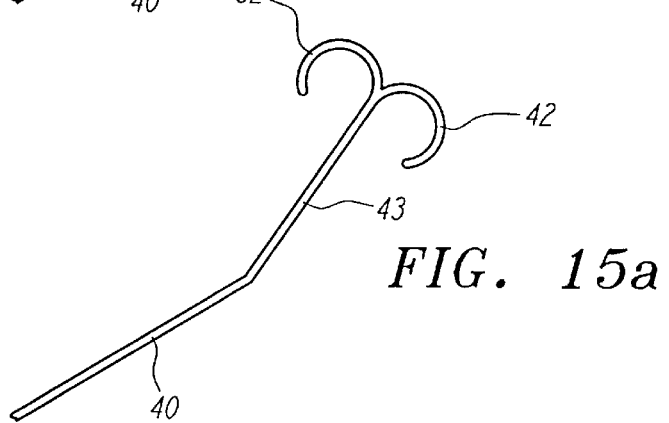

The double hooked vein harvester 51 is used in much the same manner as the hooked vein harvester 39. The first hook 42 is slipped under the saphenous vein and rotated fully so that the second hook 52 can be slipped over the saphenous vein, so that the vein is more fully surrounded by the hooks. The hooks can be made long enough to fully encircle the vein. In this case, tributary veins will obstruct the proximal hook or second hook 52 when it is pulled. When obstructed, the shaft 40 can be rotated until the second hook 52 is no longer obstructed by the tributary vein, and pulled until the second hook passes the tributary. The tributary will then block the distal hook 42, and can be passed by again rotating the shaft 40 back to its original position until the distal hook 42 is no longer obstructed, and the shaft 40 can be pulled until the distal hook 42 passes the tributary. Alternatively, the hooks can be made short enough so that they do not completely encircle the vein. In this manner, the hooks can be pulled more safely past tributary veins because a radial segment will remain open between the hooks. An alternative embodiment of the double hooked vein harvester may have both hooks located at the same point on the shaft and opposing each other, as shown in FIG. 15a.

Figure 16:
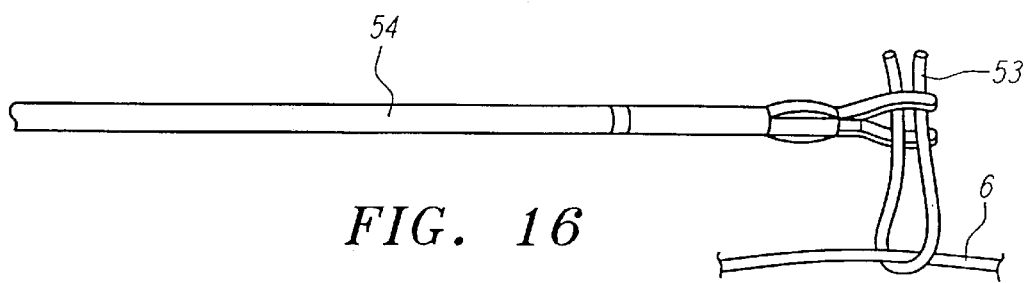
FIG. 16 shows a tube harvester.

Another device for vein harvesting is shown in FIG. 16. A soft plastic or rubber tube 53 is threaded under the saphenous vein using standard laparoscopic instruments such as laparoscopic forceps and a hooked suturing needle (not shown). After the tube has been threaded around the vein, the surgeon grasps both ends in a laparoscopic grasper 54. With the tube grasped close to the vein so that it surrounds the vein, the surgeon can pull tube along the vein to separate the vein from its connective tissue and lift it from its channel. Tributaries are detected when the surgeon feels more resistance to pulling on the tube. The tube may be made of any material which is pliant enough to thread around the vein and pulled along the vein without injuring the vein.

Figure 19:
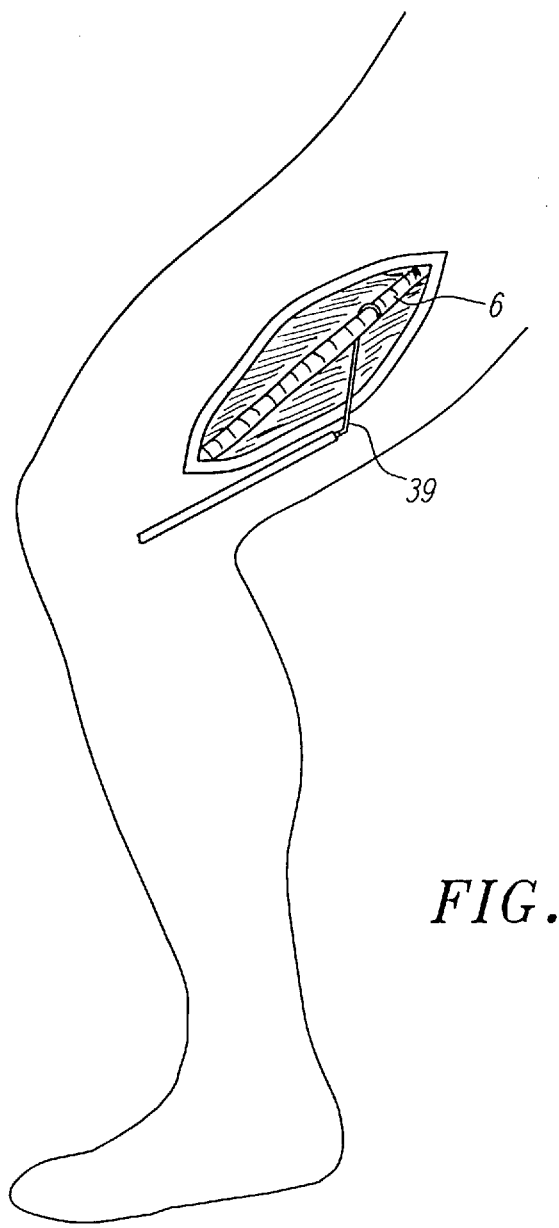
FIG. 19 illustrates the use of a hooked vein harvester during open harvesting of the saphenous vein.

Some of the advantages of the vein harvester may be beneficial during open surgery as well as endoscopic vein harvesting. FIG. 19 illustrates use of the hooked vein harvester during open harvesting of the saphenous vein. The long open incisions are made, as shown, to expose the saphenous vein. The vein harvester may be used as shown, slipped under the saphenous vein and pulled along the vein, rotated and pushed and pulled as necessary to dissect the vein from its connective tissue. The saphenous vein is then separated from the tributary veins or side branches using standard surgical instruments.

The device and method described above has been developed in the field of vein harvesting and vascular surgery. However, it is readily apparent that the devices and methods may be used for dissecting and mobilizing other long organs of the body. Various arteries and veins must be dissected and mobilized for other operations, such as popliteal bypass, or a dialysis vein loop. In these operations, a vein must be harvested, and the sites at which the vein will be attached or amostosized must also be uncovered. The balloon dissector may also be used to gain access to any blood vessel for any type of vascular surgery. For example, communicating veins or perforators in the calf may be exposed by dissecting the muscles deep within the calf to expose these blood vessels to accomplish a Linton procedure endoscopically. The vein harvesting methods may be used to dissect and mobilize those portions of the arteries to which grafts will be placed. Other vessels may be dissected from surrounding tissue, such as fallopian tubes, spermatic cords, bile ducts, intestines and others. These vessels may be dissected and mobilized endoscopically using the techniques described above.

The vein harvesting devices shown above may be made from with a variety of materials. The methods shown may be applied to harvesting veins or arteries other than the saphenous vein and other veins mentioned above, and may be employed for harvesting veins for transplant into any area of the body. Where appropriate, the devices and methods may be used during open surgery to facilitate the removal of veins or arteries, in which case the working space is provided by normal open surgery techniques. While the preferred embodiments of the devices and methods have been described, they are merely illustrative of the principles of the invention. Other embodiments and configurations may be devised without departing from the spirit of the inventions and the scope of the appended claims.

What is claimed is:

1. A device for dissecting an elongate structure from surrounding connective tissue, said device comprising:

a long slender shaft having a distal end and a proximal end and defining a longitudinal axis, said distal end having a first sideways hook, said sideways hook lying in a plane substantially perpendicular to said longitudinal axis, said first sideways hook having an arc of appropriate radius to accommodate the diameter of the elongate structure and allow the elongate structure to lie within said arc of said first sideways hook.

2. The device of claim 1 further comprising:

an opposing sideways hook formed on said distal end of said shaft near said first sideways hook, said opposing sideways hook extending from the shaft in opposing relationship to said first sideways hook, and longitudinally spaced apart from said first sideways hook along said shaft.

3. A device for dissecting a blood vessel from surrounding connective tissue, said device to be operated through a lumen in a cannula inserted through a small incision in the body, said device comprising:

a long slender shaft having a distal end and a proximal end defining a longitudinal axis and a predetermined cross-section and shape, said distal end having a first sideways hook, said sideways hook lying in a plane substantially perpendicular to said longitudinal axis, said first sideways hook having an arc of appropriate radius to accommodate the diameter of the blood vessel and allow the blood vessel to lie within said arc of said first sideways hook.

4. The device of claim 3 further comprising:

an opposing sideways hook formed on said distal end of said long slender shaft near said first sideways hook, said opposing sideways hook extending from said shaft in opposing relationship to said first sideways hook, and longitudinally spaced apart from said first sideways hook along said shaft.

5. A device for dissecting an elongate structure from surrounding connective tissue, said device comprising:

a long slender shaft having a distal end and a proximal end, said distal end having a first sideways hook, said first sideways hook having a first arc of appropriate radius to accommodate the diameter of the elongate structure and allow the structure to lie within said arc of said first sideways hook; and an opposing sideways hook formed on said distal end of said shaft, said opposing sideways hook extending from the shaft in opposing relationship to said first sideways hook, said opposing sideways hook defining an arc having a center point in spaced apart relation to a center point of said first arc.

6. A device for dissecting an elongate structure from surrounding connective tissue, said device comprising:

a long slender shaft having a distal end and a proximal end and a predetermined cross-section and shape, said distal end having a fist sideways hook, said first sideways hook having a first arc of appropriate radius to accommodate the diameter of the elongate structure and allow the structure to lie within said arc of said first sideways hook; and an opposing sideways hook formed on said distal end of said shaft, said opposing sideways hook extending from the shaft in opposing relationship to said first sideways hook, said opposing sideways hook defining an arc having a center point in spaced apart relation to a center point of said first arc.

* * * * *

UNITED STATES PATENT AND TRADEMARK OFFICE
CERTIFICATE OF CORRECTION

PATENT NO      :   5,876,413
DATED          :   March 2, 1999
INVENTOR(S)    :   Thomas J. Fogarty et al.

It is certified that error appears in the above-identified patent and that said Letters Patent are hereby corrected as shown below:

Column 1, line 10, please change "entirely" to -- entirety --.

Column 9, line 61, please change "pull tube" to -- pull the tube --.

Column 11, line 33, please delete "from".

Column 12, line 46, please change "fist" to --- first --.

Signed and Sealed this

Twenty-second Day of May, 2001

Attest:

NICHOLAS P. GODICI

Attesting Officer

Acting Director of the United States Patent and Trademark Office